United States Patent [19]

Brown et al.

[11] 4,089,674
[45] May 16, 1978

[54] SELECTIVE HERBICIDES

[75] Inventors: Michael Joseph Brown, Woodley; David Cartwright, Reading; David John Collins, Ascot; Brian Graham White, Crowthorne, all of England

[73] Assignee: Imperial Chemical Industries Limited, London, England

[21] Appl. No.: 680,125

[22] Filed: Apr. 26, 1976

[30] Foreign Application Priority Data

Apr. 28, 1975 United Kingdom ............... 17513/75

[51] Int. Cl.² ...................... A01N 9/22; C07D 401/02
[52] U.S. Cl. ................. 71/94; 260/294.8 C; 260/294.9; 260/295 R; 260/296 D
[58] Field of Search ........................... 71/94

[56] References Cited

U.S. PATENT DOCUMENTS

| 2,972,528 | 2/1961 | Brian et al. | 71/94 |
| 3,326,926 | 6/1967 | Homer | 71/94 X |
| 3,332,959 | 7/1967 | Braunholtz | 71/94 X |
| 3,449,110 | 6/1969 | Crowdy et al. | 71/92 |
| 3,671,213 | 6/1972 | White | 71/92 |
| 3,905,986 | 9/1975 | Colchester et al. | 71/94 X |
| 3,920,443 | 11/1975 | Drewe et al. | 71/94 |

FOREIGN PATENT DOCUMENTS 991,288 5/1965 United Kingdom ..................... 71/94

*Primary Examiner*—Joseph Paul Brust
*Attorney, Agent, or Firm*—Cushman, Darby & Cushman

[57] ABSTRACT

A process of selectively killing or severely damaging oats growing in cereal crops other than oats by applying to the crop area, in an amount sufficient to kill or severely damage the oats, but insufficient to damage the cereal crop substantially, a 4,4'-bipyridylium diquaternary salt.

4 Claims, No Drawings

SELECTIVE HERBICIDES

This invention relates to herbicidal processes.

According to the present invention, there is provided a process of selectively killing or severely damaging oats (plants of the genus Avena) growing in cereal crops other than oats, which comprises applying to the crop area, in an amount sufficient to kill or severely damage the oats, but insufficient to damage the crop substantially, a 4,4'-bipyridylium diquaternary salt of the formula:

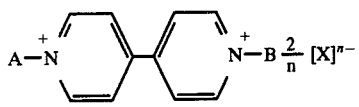

wherein $X^-$ represents an anion, $n$ is 1, 2, 3 or 4, and A and B, which may be the same or different, each stand for a substituted or unsubstituted alkyl or alkenyl group, the number of carbon atoms in the alkyl or alkenyl groups of A and B taken together being at least four, and the substituents being selected from cyano, halogen, ethynyl (CH≡C—), alkynyl, hydroxy, alkoxy, alkoxycarbonyl, alkylthio, oximino (=N.OH), acylamido and alkoxycarbonylamino.

In the foregoing list of substituents, the term "acyl" occurring in the term "acylamido" includes for example acyl groups derived from alkanoic acids, for example acetyl, propionyl and butyryl radicals. The term "alkyl" in the list of substituents includes, for example, alkyl groups of from 1 to 6 carbon atoms. The term "alkynyl" includes, for example, alkynyl radicals containing from 3 to 6 carbon atoms. The term "alkoxy" either on its own or as part of the terms "alkoxycarbonyl" or "alkoxycarbonylamino" includes, for example, alkoxy groups of 1 to 6 carbon atoms.

The total number of carbon atoms in the alkyl or alkenyl groups of A and B taken together may be, for example, from 4 to 10 or more; the total may be for example 6, 7 or 8 carbon atoms. These totals exclude, of course, carbon atoms which may be present in the substituents when A or B is a substituted alkyl or alkenyl group.

As specified above, the groups A and B may be the same or different. The compounds useful in the process of the invention therefore include, for example, compounds in which both A and B represent the same alkyl group. Examples of this group of compounds include compounds in which A and B represent propyl, butyl, or pentyl radicals. Examples of compounds in which A and B represent different alkyl radicals include compounds in which A and B are selected from methyl, ethyl, propyl, butyl, cyclopropylmethyl, pentyl and isopentyl radicals, the radicals being selected to make up a total of at least four carbon atoms, as hereinbefore provided, and preferably not more than ten.

Compounds in which A and B both represent the same alkenyl radical include for example those in which the alkenyl radical is 2-butenyl, 3-butenyl, 2-methylallyl, 2-ethylallyl, 2-propylally, or 2-methyl-2-butenyl.

Compounds in which A is an alkyl radical and B is an alkenyl radical include for example those in which A is selected from methyl, ethyl, propyl and cyclopropylmethyl, and B is selected for example from allyl, 2-methylallyl, 2-ethylallyl, 2-propylallyl, 2-methyl-2-butenyl, 2-butenyl, 3-butenyl and 4-pentenyl.

Compounds in which A is a substituted alkyl radical and B is an alkenyl radical include for example those in which A is selected from 2-methoxyethyl, 2-ethoxyethyl, 3-hydroxypropyl, 3-ethoxypropyl, 3-cyanopropyl, 3-fluoropropyl, 3-chloropropyl and 3-bromopropyl and B is selected from allyl, 2-methylallyl, 2-ethylallyl, 2-butenyl, 3-butenyl and 4-pentenyl.

Compounds in which A is a substituted alkyl radical and B is an unsubstituted alkyl radical include for example those in which A is selected from 2-acetamidoethyl, 2-N-methylacetamidoethyl, 2-ethoxyethyl, 2-methoxyethyl, 3-cyanopropyl, 3-ethoxypropyl, 3-fluoropropyl, 3-methoxypropyl, 3-allyloxypropyl, 3-hydroxypropyl, 2-hydroxyiminopropyl, 3-ethoxycarbonylaminopropyl, 3-bromobutyl, or 3-methoxybutyl radical, and B is an ethyl, propyl, butyl, cyclopropylmethyl, or pentyl radical.

Particular examples of compounds useful in the process of the invention are listed in Table I below.

TABLE I

| COMPOUND NO | A | B | Y | Z | MELTING* POINT ° C |
|---|---|---|---|---|---|
| 1 | $nC_3H_7$ | $nC_3H_7$ | Br | Br | 260–270 |
| 2 | $CH_3$ | $nC_4H_9$ | Br | I | 265–270 |
| 3 | $isoC_3H_7$ | $isoC_3H_7$ | I | I | 270–275 |
| 4 | —CH₃CH=CH₂ (with CH₃) | —CH₂C=CH₂ (with CH₃) | Cl | Cl | 240–280 |
| 5 | —CH₂CH=CHCH₃ | —CH₂CH=CHCH₃ | Br | Br | 195–200 |
| 6 | —CH₂CH=CH₂ | —CH₂C=CH₂ (with CH₃) | Br | Cl | 230–234 |
| 7 | —CH₂CH₂CH=CH₂ | —CH₂CH₂CH=CH₂ | Br | Br | 240–250 |
| 8 | $C_2H_5$ | —CH₂C=CH₂ (with CH₃) | I | I | 209 |
| 9 | —CH₂—◁ | —CH₂—◁ | Br | Br | 265 |
| 10 | —CH₂—◁ | —CH₂CH=CH₂ | Br | Br | 231 |
| 11 | $CH_3$ | $—C_3H_7$ | Br | I | 255–260 |
| 12 | $CH_3$ | $C_5H_{11}$ | Br | I | 250–255 |

TABLE I-continued

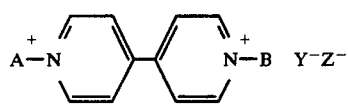

| COMPOUND NO | A | B | Y | Z | MELTING POINT °C |
|---|---|---|---|---|---|
| 13 | $C_2H_5$ | $-CH_2-\triangleleft$ | Br | I | 214–218 |
| 14 | $C_3H_7$ | $-CH_2CH=CH_2$ | Br | Br | 223–225 |
| 15 | $C_4H_9$ | $CH_2CH=CH_2$ | Br | Br | 224–226 |
| 16 | $-CH_2CH=CH_2$ | $-(CH_2)_3Cl$ | Br | Br | 290 |
| 17 | $-CH_2CH=CH_2$ | $-CH_2CH=CHCH_3$ | Br | Br | 205 |
| 18 | $-CH_2CH=\overset{CH_3}{\underset{|}{C}}-Cl$ | $-CH_2CH=\overset{CH_3}{\underset{|}{C}}-Cl$ | Cl | Cl | 200 |
| 19 | $C_2H_5$ | $C_3H_7$ | Br | I | 240–250 |
| 20 | $C_3H_7$ | $-CH_2\overset{CH_3}{\underset{|}{C}}=CH_2$ | 1.5 Br | 0.5 Cl | 245–248 |
| 21 | $-CH_2\overset{CH_3}{\underset{|}{C}}=CHCH_3$ | $-CH_2\overset{CH_3}{\underset{|}{C}}=CHCH_3$ | Br | Br | 255–260 |
| 22 | $-CH_2\overset{C_2H_5}{\underset{|}{C}}=CH_2$ | $-CH_2\overset{C_2H_5}{\underset{|}{C}}=CH_2$ | Br | Br | 255–260 |
| 23 | $C_2H_5$ | $-CH_2\overset{CH_3}{\underset{|}{C}}=CHCH_3$ | Br | Br | 197–198 |
| 24 | $CH_3$ | $-CH_2\overset{CH_3}{\underset{|}{C}}=CHCH_3$ | 1.5 Br | 0.5 I | 218–219 |
| 25 | $C_2H_5$ | $-CH_2CH_2CH=CH_2$ | Br | Br | 236–238 |
| 26 | $CH_3$ | $-CH_2\overset{C_2H_5}{\underset{|}{C}}=CH_2$ | Br | Br | 255–260 |
| 27 | $C_2H_5$ | $-CH_2\overset{C_2H_5}{\underset{|}{C}}=CH_2$ | Br | Br | 220–225 |
| 28 | $CH_3$ | $-CH_2\overset{C_3H_7}{\underset{|}{C}}=CH_2$ | Br | Br | 245–250 |
| 29 | $CH_2CH=CH_2$ | $-CH_2CH_2CH=CH_2$ | Br | Br | 228–230 |
| 30 | $C_2H_5$ | $-CH_2\overset{Cl}{\underset{|}{C}}=CH_2$ | Br | Cl | 190 |
| 31 | $CH_3$ | $-CH_2CH_2CH(CH_3)_2$ | Br | I | 270–275 |
| 32 | $C_3H_7$ | $-CH_2CH_2CH=CH_2$ | Br | Br | 254–256 |
| 33 | $C_4H_9$ | $-(CH_2)_3F$ | Br | Br | 230–240 |
| 34 | $-CH_2CH=CH_2$ | $-CH_2\overset{C_2H_5}{\underset{|}{C}}=CH_2$ | Br | Br | 125–130 |
| 35 | $C_2H_5$ | $-CH_2\overset{C_3H_7}{\underset{|}{C}}=CH_2$ | Br | Br | 225–230 |
| 36 | $CH_2CH=CH_2$ | $-(CH_2)_3Br$ | Br | Br | over 300 |
| 37 | $C_2H_5$ | $C_5H_{11}$ | Br | Br | 235–237 |
| 38 | $C_2H_5$ | $-CH_2CH=CHCH_3$ | Br | Br | 190–195 |
| 39 | $C_2H_5$ | $-CH_2CH=\overset{Cl}{\underset{|}{C}}CH_3$ | Cl | Cl | 195–200 |
| 40 | $CH_2CH=CH_2$ | $-CH_2CH=\overset{Cl}{\underset{|}{C}}CH_3$ | Br | Cl | 180–185 |
| 41 | $-(CH_2)_3F$ | $-CH_2\overset{CH_3}{\underset{|}{C}}=CH_2$ | Br | Cl | 211–213 |
| 42 | $-(CH_2)_3F$ | $-CH_2CH_2CH=CH_2$ | Br | Br | 244–246 |
| 43 | $-CH_2CH_2OCH_3$ | $-CH_2\overset{C_2H_5}{\underset{|}{C}}=CH_2$ | Br | Br | 130–135 |
| 44 | $C_3H_7$ | $-CH_2CH_2OC_2H_5$ | Br | Br | 225–230 |
| 45 | $-CH_2CH_2OC_2H_5$ | $-CH_2\overset{CH_3}{\underset{|}{C}}=CH_2$ | Cl | Br | 225–230 |
| 46 | $C_3H_7$ | $-CH_2CH_2OCH_3$ | Br | Br | 165–170 |
| 47 | $C_3H_7$ | $-CH_2CH=CHCH_3$ | Br | Br | 199–202 |
| 48 | $-(CH_2)_3CN$ | $-CH_2CH=CH_2$ | Br | Br | 212–214 |
| 49 | $C_2H_5$ | $-(CH_2)_3CH=CH_2$ | Br | Br | 237–242 |
| 50 | $C_4H_9$ | $(CH_2)_3CN$ | Br | Br | 245–250 |
| 51 | $CH_2CH_2OCH_3$ | $CH_2CH=\overset{Cl}{\underset{|}{C}}CH_3$ | Br | Cl | 175–180 |
| 52 | $CH_3$ | $-(CH_2)_3CH=CH_2$ | 1.5 Br | 0.5 I | 239–241 |
| 53 | $-CH_2CH_2CH=CH_2$ | $-(CH_2)_3CN$ | Br | Br | 238–242 |
| 54 | $-CH_2CH=CH-CH_3$ | $-(CH_2)_3F$ | Br | Br | 210–215 |
| 55 | $C_3H_7$ | $CH_2CH_2OCH_2CH=CH_2$ | Br | Br | 205–210 |

TABLE I-continued $$A-\overset{+}{N}\diagdown\diagup\overset{+}{N}-B \quad Y^-Z^-$$

| COMPOUND NO | A | B | Y | Z | MELTING* POINT °C |
|---|---|---|---|---|---|
| 56 | $-CH_2CH_2C\equiv CH$ | $-CH_2CH_2C\equiv CH$ | $pCH_3 \cdot C_6H_4 \cdot SO_3$ | $pCH_3 \cdot C_6H_4 \cdot SO_3$ | 206 |
| 57 | $-(CH_2)_3OC_2H_5$ | $C_2H_5$ | Br | Br | 205–210 |
| 58 | $-CH_2CH_2OCH_3$ | $-CH_2CH_2SC_2H_5$ | Br | Br | 140 |
| 59 | $C_4H_9$ | $-(CH_2)_3OH$ | Br | Br | 265–270 |
| 60 | $-CH_2\overset{C_2H_5}{\underset{|}{C}}=CH_2$ | $-(CH_2)_3OH$ | Br | Br | 253–254 |
| 61 | $-CH_2\overset{CH_3}{\underset{|}{C}}=CH_2$ | $-(CH_2)_3OH$ | Br | Br | 245–250 |
| 62 | $C_3H_7$ | $C_4H_9$ | Br | Br | 260–265 |
| 63 | $C_2H_5$ | $-CH_2CH_2OCH_2CH=CH_2$ | Br | Br | 215–220 |
| 64 | $-(CH_2)_3CN$ | $-CH_2CH=CH-CH_3$ | Br | Br | 215–220 |
| 65 | $C_3H_7$ | $-(CH_2)_3OC_2H_5$ | Br | Br | 218 |
| 66 | $-CH_2CH_2OC_2H_5$ | $-CH_2CH=CH_2$ | Br | Br | 145–150 |
| 67 | $-CH_2-\triangleleft$ | $C_3H_7$ | Br | Br | 210–215 |
| 68 | $-(CH_2)_3F$ | $-CH_2CH_2OCH_2CH=CH_2$ | Br | Br | 194–198 |
| 69 | $C_2H_5$ | $-CH_2CH_2\overset{Br}{\underset{|}{C}}HCH_3$ | Br | Br | 210–215 |
| 70 | $-CH_2CH=CH_2$ | $-CH_2C\equiv CH$ | Br | Br | 245–250 |
| 71 | $-(CH_2)_3F$ | $-CH_2CH_2OC_2H_5$ | Br | Br | 210–213 |
| 72 | $C_4H_9$ | $-CH_2CH_2OCH_3$ | Br | Br | 245–250 |
| 73 | $-CH_2CH_2OC_2H_5$ | $-CH_2CH=CH_2$ | Br | Br | 225–230 |
| 74 | $-CH_2CH_2OCH_3$ | $-CH_2CH=CHCH_3$ | Br | Br | 200–205 |
| 75 | $-CH_2CH_2OCH_3$ | $-CH_2CH_2CH=CH_2$ | Br | Br | 245–250 |
| 76 | $-CH_2CH_2OCH_3$ | $-(CH_2)_3CH=CH_2$ | Br | Br | 225–230 |
| 77 | $-(CH_2)_3OC_2H_5$ | $-CH_2CH=CH_2$ | Br | Br | 175–180 |
| 78 | $-(CH_2)_3CN$ | $-CH_2\overset{C_2H_5}{\underset{|}{C}}=CH_2$ | Br | Br | 225–230 |
| 79 | $C_2H_5$ | $-CH_2CH=CH_2$ | 1.9 Br | 0.1 I | 214–216 |
| 80 | $C_2H_5$ | $C_4H_9$ | Br | Br | 250–252 |
| 81 | $-CH_2CH_2OC_2H_5$ | $CH_2-\triangleleft$ | Br | Br | 215–220 |

*Melting is in nearly all cases attended by decomposition.

Further examples of compounds which may be used in the process of the invention are listed in Table II.

TABLE II

| COMPOUND NO | A | B | Y | Z | MELTING* POINT °C |
|---|---|---|---|---|---|
| 82 | $C_5H_{11}$ | $-(CH_2)_3OH$ | Br | Br | 250–255 |
| 83 | $CH_2-\triangleleft$ | $-CH_2CH_2OCH_2CH=CH_2$ | Br | Br | 210 |
| 84 | $C_3H_7$ | $-CH_2CH_2\overset{OCH_3}{\underset{|}{C}}HCH_3$ | Br | Br | 250 |
| 85 | $-CH_2CH=CH_2$ | $-CH_2CH_2SC_2H_5$ | Br | Br | 205 |
| 86 | $-CH_2CH=CH_2$ | $-CH_2CH_2\overset{OCH_3}{\underset{|}{C}}HCH_3$ | Br | Br | 210 |
| 87 | $-CH_2-\triangleleft$ | $-CH_2CH_2C\equiv CH$ | Br | Br | 265–270 |
| 88 | $C_2H_5$ | $-CH_2CH_2\overset{OCH_3}{\underset{|}{C}}HCH_3$ | Br | Br | 220 |
| 89 | $-CH_2CH_2CH=CH_2$ | $-CH_2CH_2OC_2H_5$ | Br | Br | 234–235 |
| 90 | $-CH_2CH_2C\equiv CH$ | $-CH_2CH_2CH=CH_2$ | Br | Br | over 270 |
| 91 | $C_3H_7$ | $-CH(CH_3)_2$ | Cl | Cl | 260 |
| 92 | $C_3H_7$ | $-CH_2CH(CH_3)_2$ | Cl | Cl | 260 |
| 93 | $-CH_2CH(CH_3)_2$ | $-CH_2CH(CH_3)_2$ | Cl | Cl | over 260 |
| 94 | $C_2H_5$ | $-CH_2CH(CH_3)_2$ | Cl | Cl | 255–260 |
| 95 | $-CH_2CH(CH_3)_2$ | $-CH_2CH_2CH_2CN$ | Cl | Cl | 250–255 |
| 96 | $C_3H_7$ | $-(CH_2)_3F$ | Br | Br | 255–260 |
| 97 | $-CH(CH_3)_2$ | $-CH_2\overset{CH_3}{\underset{|}{C}}=CH_2$ | Cl | Cl | 215–220 |
| 98 | $CH_3\overset{}{\underset{\|\!\!\!O}{C}}NHCH_2CH_2-$ | $C_5H_{11}-$ | Br | Cl | 220–225 |
| 99 | $C_2H_5-$ | $sec-C_4H_9$ | Cl | Cl | 260–265 |
| 100 | $C_4H_9-$ | $-CH_2CH_2\overset{CH_3}{\underset{|}{N}}CCH_3\underset{\|\!\!\!O}{}$ | Br | Cl | 250–255 |

TABLE II-continued

| COMPOUND NO | A | B | Y | Z | MELTING* POINT °C |
|---|---|---|---|---|---|
| 101 | $C_2H_5-$ | $-CH_2CH=C\begin{smallmatrix}CH_3\\CH_3\end{smallmatrix}$ | Br | Cl | 200–205 |
| 102 | $C_4H_9-$ | $-CH_2-\underset{\mid}{C}=NOH$ with $CH_3$ | Br | Cl | 215–220 |
| 103 | $C_3H_7-$ | $-CH_2CH=CH-\underset{\underset{O}{\|\|}}{C}OCH_3$ | Br | Br | 185–190 |
| 104 | $C_3H_7-$ | $-(CH_2)_3NH\underset{\underset{O}{\|\|}}{C}OC_2H_5$ | Cl | Cl | 210–212 |

*Melting is in nearly all cases attended by decomposition.
N.B. The melting points quoted for compounds 91, 92, 93, 94 and 97 are for the diiodide salts of these compounds. The melting point quoted for compound 95 is for the hemi-iodo-sesquibromide salt.

The salt of the 4,4'-bipyridylium cation may be formed from two identical anions [X]$^{n-}$ or from mixtures of different anions. A salt having any particular desired anion may be prepared either by direct synthesis from reactants which include the desired anion, or by exchanging the anion of a previously prepared salt for the preferred anion by methods well known in the art, for example by passing a solution of the previously prepared salt through an ion exchange resin loaded with the required anion. Preferably the anion is one which gives rise to a salt of high water-solubility, so that water solutions containing for example at least 100 grams per liter of the bipyridylium cation may be prepared. For reasons of convenience and economy, bromide or chloride anions are preferred, particularly the chloride anion. Other anions which may be used include methosulphate, sulphate and nitrate.

Since the characteristic herbicidal activity of a 4,4'-bipyridylium diquaternary salt resides in the cation only, it is customary to quote concentrations of active ingredient and rates of application in terms of the amount of bipyridylium quaternary cation used, thus avoiding the inconvenience of having to quote different application rates for different salts of the same bipyridylium quaternary cation. Application rates and concentrations quoted in this specification therefore relate to the amount of bipyridylium quaternary cation unless otherwise stated.

In practising the process of the invention, the rate at which the bipyridylium quaternary cation is applied will depend upon which cation is selected for use, but a rate of from 0.25 to 10.0 kilograms per hectare is usually suitable. Rates of from 0.25 to 3 kilograms per hectare are preferred. Although the principal feature of the present invention is a method of controlling the growth of oat species in cereals other than oats, the bipyridylium quaternary cations used in the invention also severely damage or kill a wide range of other weeds, for example those in the following list:
Senecio vulgaris
Ipomoea purpurea
Amaranthus retroflexus
Polygonum aviculare
Chenopodium album
Portulaca oleracea
Digitaria sanguinalis
Eleusine indica
Poa annua The compounds used in the process of the invention may be prepared by conventional methods well known to those skilled in the art. Compounds in which A and B, are the same, for example, may be prepared as illustrated in Example 5 by mixing 4,4'-bipyridyl with the stoichiometric amount or a slight excess of the appropriate quaternising agent and heating the mixture to a suitable temperature for sufficient time to bring about the quaternising reaction. Usually the temperature required will be in the range from 50° to 150° C but lower or higher temperatures may also be employed. Usually a diluent or solvent is mixed with the reactants in order to moderate the vigour of the reaction, should this prove to be strongly exothermic. Examples of diluents and solvents include water, methanol, ethanol, n and iso propanol, and dimethylformamide.

Compounds in which A and B are different are prepared in two stages, as illustrates in Examples 4 and 6. In the first stage, 4,4'-bipyridyl together with the calculated quantity of quaternising agent to form the monoquaternary salt of formula

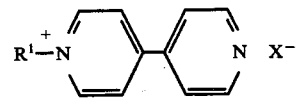

wherein R$^1$ represents a quaternising substituent A or B as hereinbefore defined, is dissolved in a solvent in which quaternary salts are usually insoluble, for example toluene or acetone. The solution is left to stand, or if desired, heated to accelerate the reaction, and the quaternary salt which separates out is collected and if necessary purified by recrystallisation. The monoquaternary salt so obtained is then dissolved in a further solvent, for example water, a lower alcohol, or dimethylformamide, and the calculated quantity of the second quaternising agent added. The solution may then be left to stand to allow the quaternisation of the second nitrogen atom of the 4,4'-bipyridyl to proceed, or may be heated to accelerate the reaction. The diquaternary 4,4'-bipyridylium salt may be isolated by conventional methods. It may for example separate from the reaction mixture on cooling, or may be isolated by evaporation of the solvent from the reaction mixture.

Where the quaternary salt is one in which A and B are different, the second quaternising agent may provide an anion different from the first. In such cases, the 4,4'-bipyridylium diquaternary salt may comprise a mixture of different anions X$^-$. The mixture may be in non-stoichiometric proportions, as in compounds 20, 24 and 52 of Table I.

With the exception of compounds no. 1 and 11, the compounds listed in Table I and II are believed to be new, and therefore form a further feature of the present invention.

For application to plants, the compounds used in the invention are preferably dissolved in water and sprayed on to the plants as dilute aqueous solutions. Preferably the spray solution contains one or more surface-active agents. The solution may also contain a humectant, that is to say a substance which tends to absorb moisture from air. The presence of the humectant tends to prevent the spray deposits on plant leaves from becoming completely dry, and may thereby assist the penetration of the bipyridylium quaternary cation into the plant.

In order to facilitate the use of the bipyridylium quaternary salts as herbicides, they may be formulated as concentrated aqueous solutions, containing a surface-active agent and optionally a humectant. These concentrated solutions may be conveniently transported and stored, and may readily be diluted with water to provide a dilute solution suitable for spraying when required. In another aspect, therefore, the invention provides herbicidal compositions comprising an aqueous solution of a salt of one or more of the quaternary cations listed in Table I and Table II, other than compounds 1 and 11 containing a surface-active agent and, optionally, a humectant. Dilute compositions suitable for spraying may contain, for example, from 1 to 20 grams per liter of the bipyridylium quaternary cation used as the active ingredient while concentrated compositions may, for example, contain from 100 to 300 grams per liter.

When a humectant is included in the composition, the amount may be varied, but may for example be from half a part to one part by weight per part of the bipyridylium quaternary cation in the composition. Examples of humectants include propylene glycol, glycerol, and calcium chloride.

The amount of surface-active agent used may also be varied; by way of example, an amount of from 0.2 to 2 parts by weight per part of bipyridylium quaternary cation is usually convenient.

The surface-active agents used in the compositions of the invention are preferably non-ionic or cationic, since anionic surface-active agents may interact with the bipyridylium quaternary cations and reduce their efficacy as herbicides. By way of example, non-ionic surface-active agents useful in the compositions of the invention include the condensation products of ethylene oxide with fatty alcohols such as oleyl alcohol and cetyl alcohol, or with alkyl phenols such as octylphenol, nonylphenol and octylcresol. A preferred non-ionic surfactant is Tergitol 15.S12, which comprises a condensate of a $C_{15}$ linear alcohol with 12 moles of ethylene oxide. Other non-ionic agents are the partial esters derived from long chain fatty acids and hexitol anhydrides, for example sorbitan monolaurate; the condensation products of the said partial esters with ethylene oxide; and the lecithins. Examples of cationic surface active agents include quaternary salts and condensates of ethylene oxide with amines, for example the substances sold under the Trade Mark "Ethomeen," "Ethoduomeen," "Duoquad" and "Arquad."

The bipyridylium salts used in the invention may be used to control both wild oats (e.g. *Avena fatua*) and cultivated oats growing in cereal crops. Cultivated oats may appear among other cereals as a result of seeds left in the soil from a previous crop of oats.

The invention is illustrated by the following Examples.

EXAMPLE 1

This Example illustrates the herbicidal activity of compounds used in the process of the invention towards oats and includes the results of applying the compounds at the same rates to barley and wheat, for comparison. The compounds were dissolved in water containing 1 gram per liter of "Lissapol" ("Lissapol" is a Trade Mark for a surface-active agent comprising a condensate of from seven to eight molar proportions of ethylene oxide with one molar proportion of p-nonylphenol) and sprayed in a volume of 1000 liters per hectare on to young barley and cultivated oat plants grown in pots. Rates of application given in Table III refer to kilograms of bipyridylium cation applied per hectare. Damage to the plants was assessed 14 days after spraying, on a scale of 0 to 5 where 0 is 0 to 20% damage and 5 is kill. Results are given in Table III below.

The results given in Table IV are for similar tests conducted with young barley, wheat and wild oat plants grown in pots. In these tests, the damage to the plants was assessed 28 days after spraying, on a scale of 0 to 10 where 0 is no effect and 10 is complete kill.

TABLE III

| COMPOUND NO | RATE OF APPLICATION kg/ha | BARLEY | OATS |
|---|---|---|---|
| 1 | 0.5 | 0 | 3 |
| 2 | 0.5 | 1 | 3 |
| 3 | 1 | 0 | 3 |
| 4 | 2 | 1 | 4 |
| 5 | 5 | 1 | 3 |
| 6 | 1 | 0 | 4 |
| 7 | 2 | 1 | 4 |
| 8 | 1 | 1 | 4 |
| 9 | 2 | 1 | 3 |
| 10 | 0.5 | 1 | 4 |
| 11 | 0.25 | 1 | 4 |
| 12 | 2 | 1 | 3 |
| 13 | 1 | 1 | 4 |
| 15 | 1 | 0 | 4 |
| 16 | 1 | 1 | 4 |
| 17 | 0.5 | 1 | 3 |
| 19 | 0.5 | 1 | 4 |
| 20 | 1 | 0 | 4 |
| 24 | 5 | 1 | 4 |
| 26 | 5 | 2 | 4 |
| 27 | 1 | 0 | 3 |
| 28 | 2 | 0 | 2 |
| 29 | 1 | 1 | 3 |
| 30 | 1 | 1 | 3 |
| 31 | 2 | 1 | 2 |
| 33 | 2 | 0 | 4 |
| 34 | 2 | 0 | 4 |
| 35 | 5 | 2 | 4 |
| 38 | 1 | 0 | 4 |
| 40 | 2 | 2 | 3 |
| 41 | 1 | 1 | 4 |
| 44 | 1 | 2 | 4 |
| 45 | 2 | 1 | 2 |
| 46 | 0.25 | 0 | 3 |
| 49 | 1 | 1 | 4 |
| 50 | 1 | 0 | 3 |
| 51 | 1 | 0 | 3 |

TABLE IV

| COMPOUND NO | RATE OF APPLICATION kg/ha | WHEAT | BARLEY | WILD OATS |
|---|---|---|---|---|
| 57 | 1 | 1 | 2 | 7 |
| 60 | 2 | 4 | 1 | 9 |
| 61 | 2 | 2 | 0 | 10 |
| 65 | 2 | 1 | 1 | 10 |
| 67 | 1 | 3 | 1 | 6 |
| 69 | 2 | 1 | 0 | 7 |
| 71 | 1 | 2 | 0 | 9 |
| 72 | 2 | 4 | 1 | 8 |
| 73 | 1 | 3 | 1 | 9 |
| 74 | 1 | 3 | 1 | 9 |
| 75 | 1 | 2 | 0 | 10 |
| 77 | 0.5 | 4 | 0 | 6 |
| 78 | 2 | 1 | 0 | 6 |

TABLE IV-continued

| COMPOUND NO | RATE OF APPLICATION kg/ha | WHEAT | BARLEY | WILD OATS |
|---|---|---|---|---|
| 81 | 2 | 0 | 1 | 8 |
| 86 | 4 | 1 | 3 | 10 |
| 87 | 4 | 0 | 1 | 7 |
| 88 | 4 | 2 | 8 | 10 |
| 89 | 4 | 0 | 1 | 10 |
| 90 | 4 | 0 | 9 | 5 |
| 91 | 1 | 4 | 3 | 7 |
| 92 | 4 | 2 | 2 | 8 |
| 93 | 4 | 0 | 2 | 6 |
| 94 | 4 | 1 | 1 | 10 |
| 95 | 1 | 1 | 2 | 8 |
| 96 | 0.5 | 2 | — | 9 |
| 97 | 4 | 2 | 1 | 10 |
| 98 | 5 | — | 0 | 8 |
| 99 | 2 | 3 | 3 | 10 |
| 100 | 4 | 2 | 3 | 10 |
| 101 | 4 | 1 | 1 | 8 |
| 102 | 4 | 1 | 2 | 10 |
| 103 | 4 | 1 | 2 | 5 |
| 104 | 5 | — | 2 | 8 |

EXAMPLE 2

This Example illustrates the herbicidal activity of compounds used in the process of the invention at various rates of application. Tests were conducted in the same way as those for which results are given in Table IV of Example 1, except that the spray volume was 200 liters per hectare. The results are given in Table V.

TABLE V

| COMPOUND NO | RATE OF APPLICATION kg/ha | WHEAT | BARLEY | WILD OATS |
|---|---|---|---|---|
| 1 | 0.2 | 0 | 0 | 0 |
|   | 0.6 | 1 | 0 | 6 |
| 4 | 2 | 1 | 0 | 6 |
|   | 4 | 1 | 0 | 9 |
|   | 8 | 2 | 2 | 10 |
| 6 | 0.25 | 0 | 0 | 9 |
|   | 0.5 | 5 | 0 | 9 |
| 8 | 1 | 0 | 0 | 8 |
|   | 2 | 1 | 0 | 9 |
|   | 4 | 3 | 2 | 9 |
| 20 | 1 | 0 | 0 | 5 |
|   | 2 | 1 | 0 | 9 |

EXAMPLE 3

This Example illustrates the herbicidal effects of compounds used in the process of the invention on plant species other than those of the genus Avena. Tests were carried out in the same way as those for which results are given in Table III in Example 1. The results are given in Table VI below; they are assessed as in Table III of Example 1.

| COMPOUND NO | APPLICATION RATE kg/ha | TEST PLANTS |||||||||||||||||
|---|---|---|---|---|---|---|---|---|---|---|---|---|---|---|---|---|---|
|   |   | Sb | Rp | Ct | Pe | Sn | Ip | Am | Pa | Ca | Po | Mz | Ba | Rc | Ot | Dg | El | Pn |
| 6 | 1 | 4 | 4 | 4 | 2 | 5 | 2 | 5 | 4 | 5 | 5 | 0 | 0 | 3 | 4 | 3 | 3 | 4 |
| 8 | 1 | 5 | 4 | 2 | 1 | 5 | 1 | 5 | 4 | 5 | 5 | 3 | 1 | 3 | 4 | 5 | 4 | 4 |
| 80 | 0.25 | 5 | 4 | 5 | 3 | 4 | 1 | 5 | 3 | 5 | 5 | 0 | 0 | 3 | 4 | 1 | 3 | 2 |

The names of the test plants are as follows:-

| Sb | Sugar beet | Am | *Amaranthus retroflexus* | Rc | Rice |
| Rp | Rape | Pa | *Polygonum aviculare* | Dg | *Digitaria sanguinalis* |
| Ct | Carrot | Ca | *Chenopodium album* | El | *Eleusine indica* |
| Pe | Pea | Po | *Portulaca oleracea* | Pn | *Poa annua* |
| Sn | *Senecio vulgaris* | Mz | Maize | | |
| Ip | *Ipomoea purpurea* | Ba | Barley | | |

EXAMPLE 4

This Example illustrates the preparation of compound no. 8 of Table I.

4,4'-Bipyridyl (50 g) was dissolved in warm toluene (400 ml) and 100 ml of toluene was then distilled off. The remaining solution was cooled to 40° C, ethyl iodide (40 g) added, and the mixture stirred at 80°-90° C for 2 hours. The yellow solid which separated was washed with acetone and recrystallised from a mixture of isopropanol, industrial methylated spirit, and water. The product (1-ethyl-4-pyridinylpyridinium iodide, 30 g) was found to be pure by paper chromatography.

The monoquaternary salt so obtained (5 g) was taken up in dimethylformamide (80 ml) and heated under reflux with 2-methyl allyl chloride (10 g) for 1½ hours. The mixture was cooled and the separated solid was recrystallised, twice from n-propanol, giving 1-ethyl-1'-2-methylallyl-4,4'-bipyridylium diiodide, with a melting point of 209° C.

EXAMPLE 5

This Example illustrates the preparation of compound no. 4 of Table I.

4,4'-Bipyridyl (100 g) and 2-methylallyl chloride (290 g) were heated under reflux in isopropanol (1500 ml) for 30 hours. The mixture was then left to stand for 3 days, and the solid which separated washed with cold industrial methylated spirit and acetone, and recrystallised twice from methylated spirit, giving compound no. 4 with a melting point of 240°-280° (decomp.).

EXAMPLE 6

This Example illustrates the preparation of compound no. 6 of Table I.

4,4'-Bipyridyl (46.8 g) was taken up in acetone (600 ml), cooled to −5° C and a solution of allyl bromide (30 g) in acetone (100 ml) added slowly. The clear solution was left overnight at room temperature. The pale yellow precipitate was collected, washed with acetone and dried at 70° C. The monoquaternary salt so obtained (1.11 kg) was dissolved in hot isopropanol (7 liters) and 2-methylallyl chloride (725 g) added. The mixture was heated under reflux for 18 hours. A further quantity (275 g) of 2-methylallyl chloride was then added and the solution heated under reflux for a further 4 hours. The precipitated product (compound no. 6 of Table I, 1,278 kg) was washed with isopropanol and recrystallised from methylated spirit. Paper chromatography confirmed that the product was pure.

We claim:

1. A process of selectively killing or severely damaging oats growing in cereal crops other than oats, which comprises applying to the crop area, in an amount sufficient to kill or severely damage the oats, but insufficient to damage the crop substantially, a 4,4'-bipyridylium diquaternary salt of the formula:

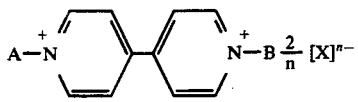

wherein X⁻ represents an essentially non-phytotoxic anion, n is 1, 2, 3 or 4, and A and B, which may be the same or different, each stand for alkyl, alkenyl, substituted alkyl or substituted alkenyl, the number of carbon atoms in the alkyl or alkenyl groups taken together being from four to ten excluding carbon atoms present in any substitution on said alkyl or alkenyl group, any such substitution being selected from the group consisting of cyano, halogen, alkynyl of 3–6 carbon atoms, hydroxyl, alkoxy of 1–6 carbon atoms, alkoxy-carbonyl wherein the alkoxy group contains 1–6 carbon atoms, alkylthio wherein the alkyl contains 1–6 carbon atoms, hydroxyimino, acylamido wherein the acyl is acetyl, propionyl or butyryl and alkoxycarbonylamino wherein the alkoxy contains 1–6 carbon atoms provided that when A or B is N-butyl, the other is not N-butyl.

2. A process according to claim 1 wherein the rate of application of the bipyridylium cation is from 0.25 to 3 kilograms per hectare.

3. A process according to claim 1 wherein the cereal crop is barley.

4. A process according to claim 3 wherein the salt is selected from the group consisting of the bromide and chloride salts of the 1-allyl-1'-(2-methylallyl)-4,4'-bipyridylium cation and said salt is applied at the rate of from 0.25 to 3 kilograms of bipyridylium cation per hectare.

* * * * *